United States Patent [19]

Gray

[11] Patent Number: 5,295,948
[45] Date of Patent: Mar. 22, 1994

[54] SPLINT/THERAPEUTIC DEVICE

[76] Inventor: James C. Gray, 2405 Alcoa Hwy., Knoxville, Tenn. 37920

[21] Appl. No.: 947,938

[22] Filed: Sep. 21, 1992

[51] Int. Cl.⁵ .................. A61F 5/00; A61F 5/37
[52] U.S. Cl. ........................... 602/5; 602/20; 602/21; 128/882
[58] Field of Search .............. 602/5, 6, 7, 8, 9, 12, 602/20, 21, 22, 27, 62-64; 128/882, 877, 878, 879, DIG. 6, 845

[56] References Cited

U.S. PATENT DOCUMENTS

| | | |
|---|---|---|
| 1,716,221 | 6/1929 | Fernie . |
| 1,726,728 | 9/1929 | Adams . |
| 3,117,786 | 1/1964 | Anderson ........................ 273/54 |
| 3,152,337 | 10/1964 | Barry ............................... 2/159 |
| 3,555,564 | 1/1971 | Miskell et al. .................... 2/168 |
| 3,581,740 | 6/1971 | Sherbourne ..................... 128/77 |
| 3,605,120 | 9/1971 | Hobbs ............................. 2/159 |
| 3,703,894 | 11/1972 | Galloway ........................ 602/21 |
| 3,779,550 | 12/1973 | Benoun et al. ................ 273/54 B |
| 3,788,307 | 1/1974 | Kistner ........................... 602/21 |
| 3,818,905 | 6/1974 | Lebold ............................ 602/21 |
| 3,903,878 | 9/1975 | Spann ............................. 602/21 |
| 3,911,497 | 10/1975 | Lewis, Jr. et al. ................. 2/16 |
| 3,944,220 | 3/1976 | Fasano ............................ 272/67 |
| 4,041,940 | 8/1977 | Frankel et al. ............... 128/80 C |
| 4,167,044 | 9/1979 | Girard ................................ 3/1 |
| 4,173,218 | 11/1979 | Cronin ........................... 128/77 |
| 4,183,098 | 1/1980 | Knowles, Jr. ...................... 2/16 |
| 4,417,570 | 11/1983 | Finnieston ...................... 128/87 |
| 4,451,044 | 5/1984 | Elliot, Jr. .................... 273/189 A |
| 4,558,694 | 12/1985 | Barber ........................... 128/87 A |
| 4,565,195 | 1/1986 | Eisenberg ...................... 128/133 |
| 4,573,456 | 3/1986 | Spann ........................... 128/80 R |
| 4,675,914 | 6/1987 | Mitchell ........................ 2/161 A |
| 4,698,850 | 10/1987 | Patton, Sr. et al. ............... 2/159 |
| 4,716,892 | 1/1988 | Brunswick ...................... 128/77 |
| 4,719,906 | 1/1988 | DeProspero ................... 128/87 A |
| 4,765,319 | 8/1988 | Finnieston et al. .......... 128/87 R |
| 4,781,178 | 11/1988 | Gordon ........................... 128/77 |
| 4,782,825 | 11/1988 | Lonardo ......................... 602/21 |
| 4,787,376 | 11/1988 | Eisenberg ...................... 128/77 |
| 4,798,199 | 1/1989 | Hubbard et al. .............. 128/87 R |
| 4,807,609 | 2/1989 | Meals ............................ 128/87 R |
| 4,883,073 | 11/1989 | Aziz .............................. 128/878 |
| 4,911,150 | 3/1990 | Farley .......................... 128/80 R |
| 4,925,187 | 5/1990 | Fleenor et al. ................ 273/54 B |
| 4,945,925 | 8/1990 | Garcia .......................... 128/877 |
| 4,949,711 | 8/1990 | Gyovai ........................... 602/21 |
| 4,960,114 | 10/1990 | Dale ............................. 128/87 R |
| 4,977,890 | 12/1990 | Mann ............................. 128/77 |

Primary Examiner—Michael A. Brown
Attorney, Agent, or Firm—Pitts & Brittian

[57] ABSTRACT

An improved splint/therapeutic device for at least partially limiting the mobility of a selected portion of a patient's body. The device (10) includes a splint body (12) fabricated of a resilient material, the splint body (12) defining an inner surface (18) for engaging the patient's body. The splint body (12) also defines a preselected thickness whereby the resilient material of the splint body biases the patient's body to a desired body position. The thickness may vary over the length and width of the splint body (12) and may be selectively reduced to increase mobility of the selected body part. The splint/therapeutic device (10) is secured to the patient's body with securing means such as tape, integrally formed body encircling portions (26'), or with securing straps (26) provided with hook-and-loop fasteners (28).

18 Claims, 4 Drawing Sheets

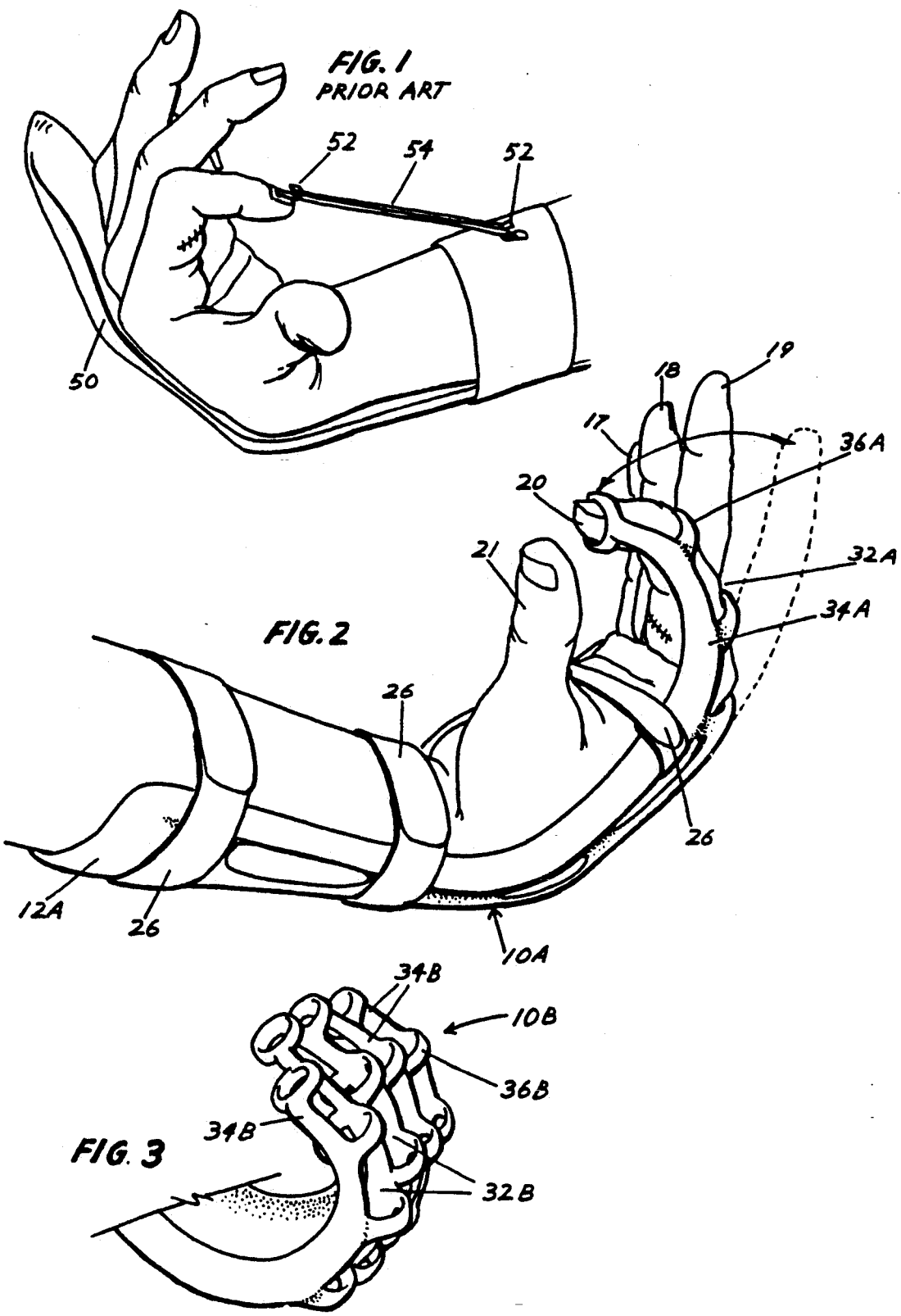

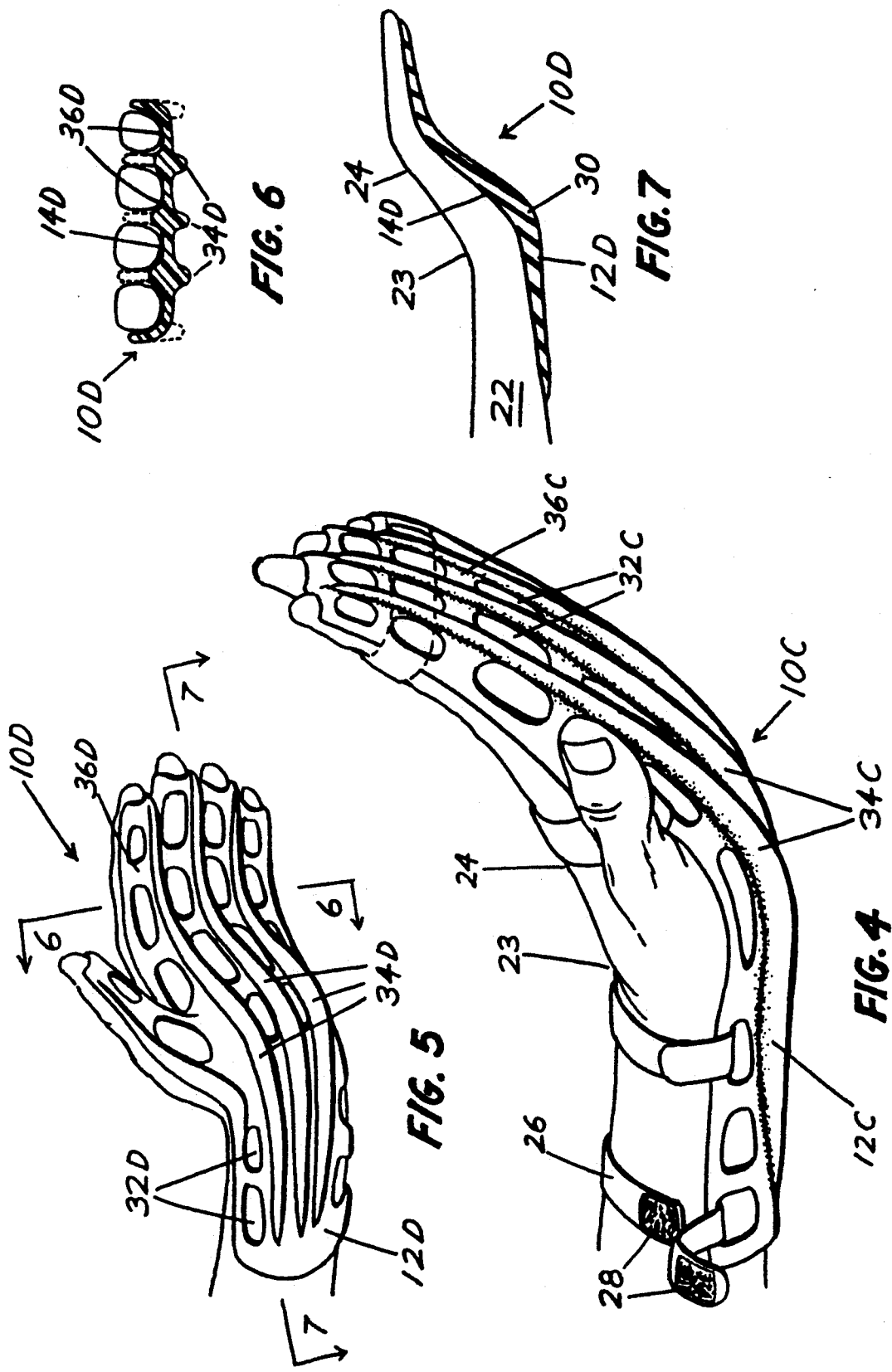

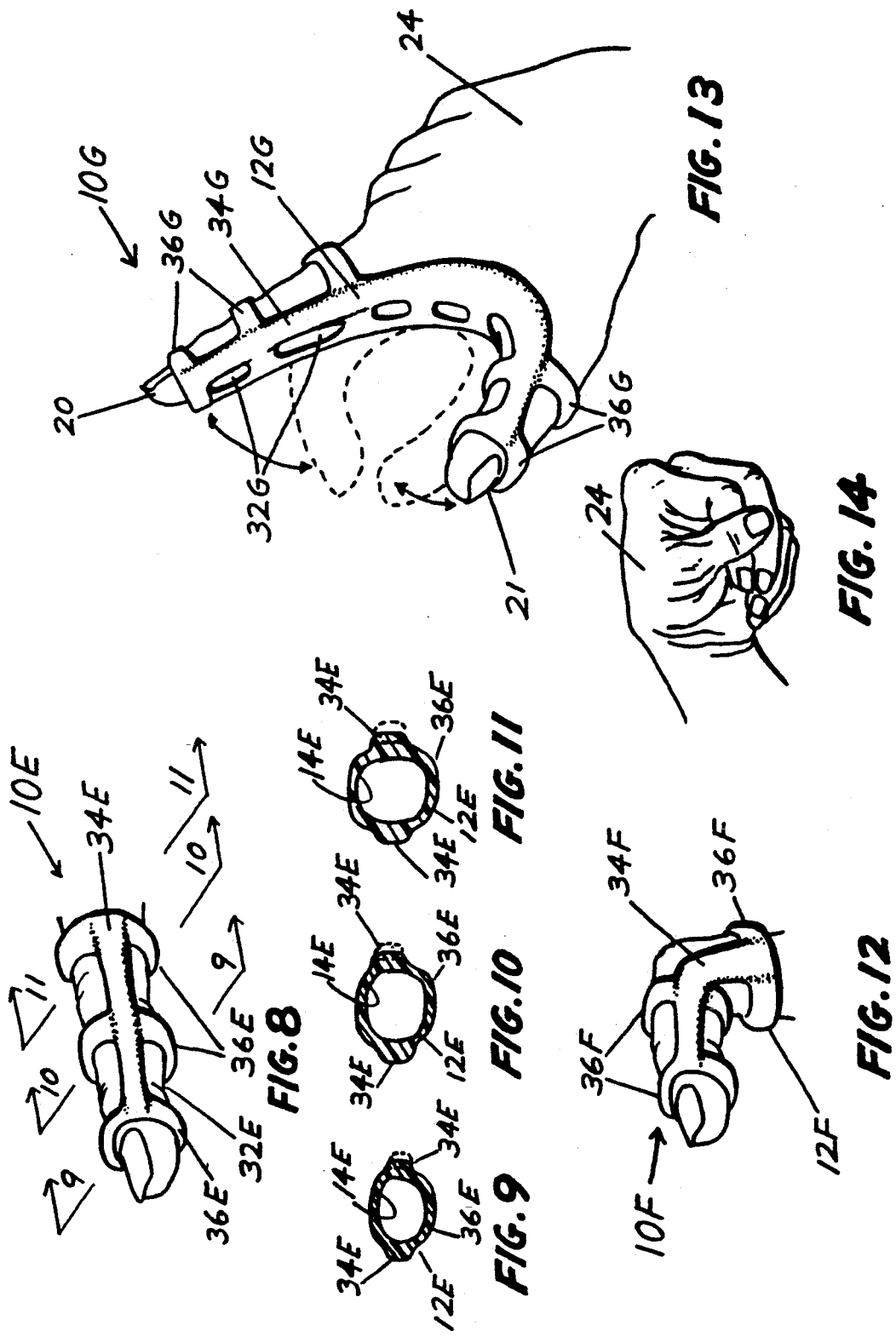

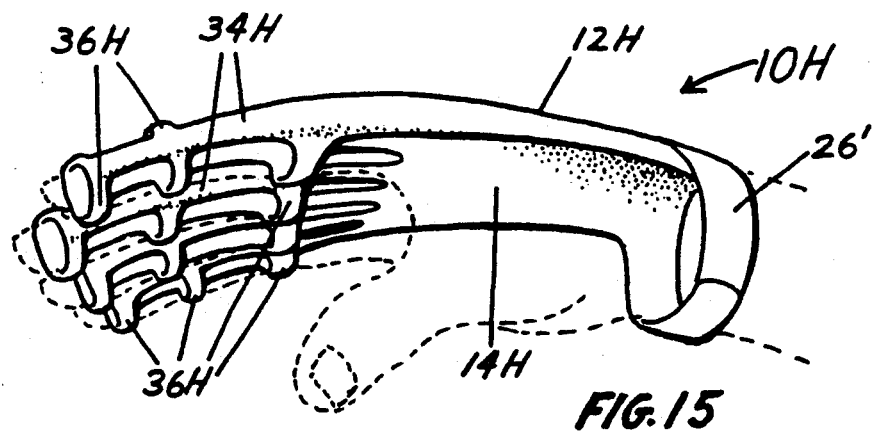
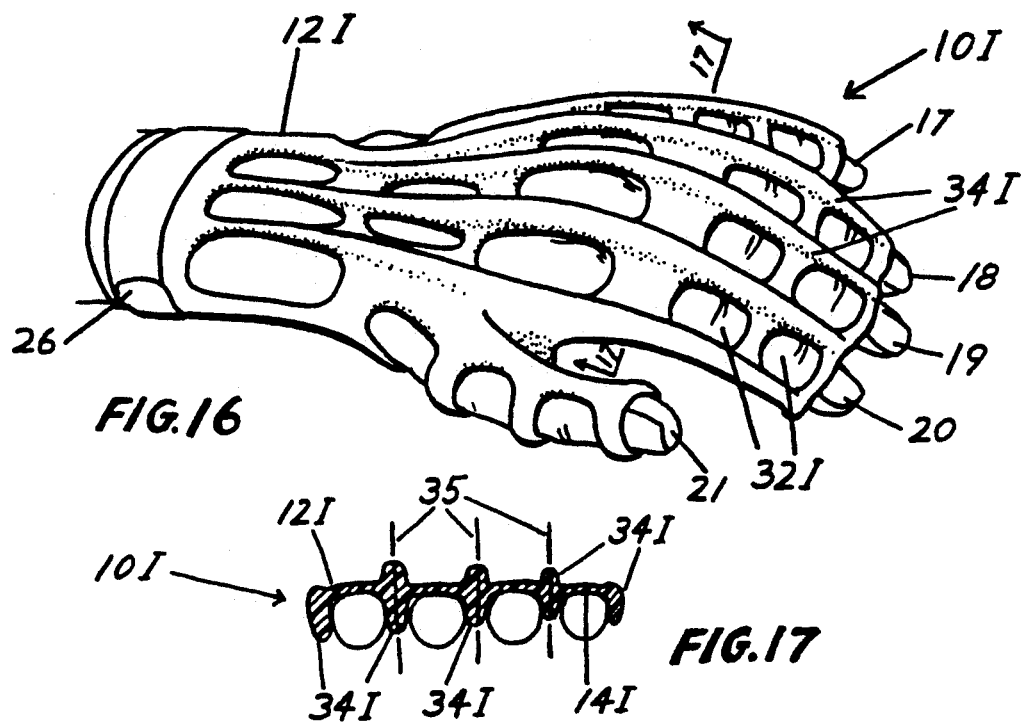
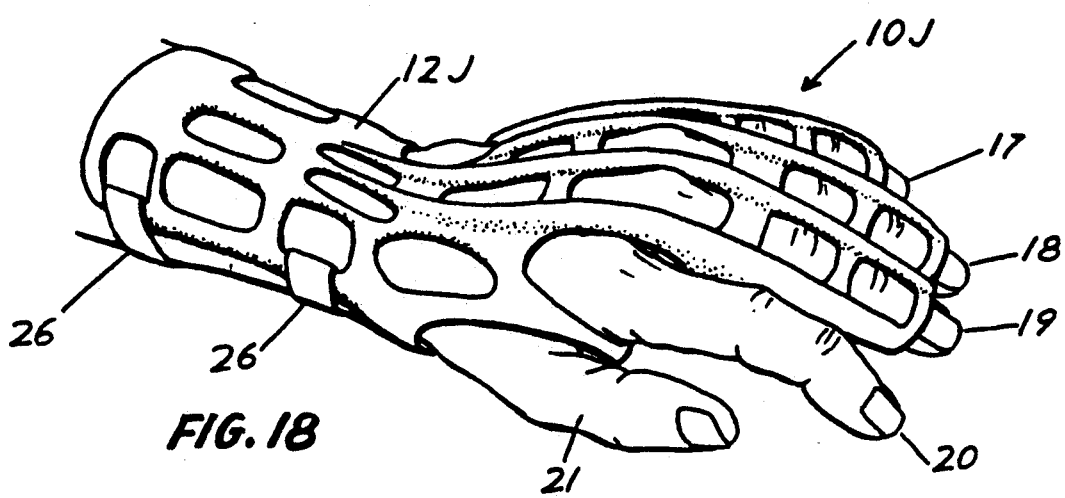

SPLINT/THERAPEUTIC DEVICE

This application in part discloses and claims subject matter disclosed in my earlier filed pending application, Ser. No. 07/633,128, filed Dec. 24, 1990, which is a continuation-in-part application of my earlier filed application, Ser. No. 07/405,657, filed Sep. 11, 1989.

TECHNICAL FIELD

This invention relates to an improved splint and therapeutic device for at least partially immobilizing selected portions of a patient's body. In this particular invention, the splint includes an integrally molded elastomeric body which selectively varies in thickness. The splint may be used to bias a selected body portion—such as a hand, a finger, or a foot—to a preselected position to aid in the healing and rehabilitation process after injury, surgery, or the like, or to assist a patient with at least partially deteriorated muscle control.

BACKGROUND ART

Splints and casts have long been used to immobilize body joints, or the ends of fractured bones. However, conventional splints and casts are generally rigid devices which are secured to the body proximate the point of an injury, and result in total immobilization of the area to which they are applied, even if total immobility is unnecessary. For example, a cast or splint applied to immobilize a fracture in the wrist quite often needlessly immobilizes the patient's fingers and/or thumb, or a cast or splint applied to immobilize a fractured bone in the forearm may needlessly result in total immobilization of the elbow joint. Moreover, for some types of injuries or deformities, total immobilization is not desirable. For example, where a hand has been deformed by osteoarthritis, it is desirable to reorient the hand to bring it to the appropriate disposition, but not desirable to totally immobilize the hand. Attempts have been made to construct splints which do allow some residual mobility such as those disclosed in U.S. Pat. Nos. 4,719,906 issued to R. DeProspero on Jan. 19, 1988; and 4,781,178 issued to K. M. Gordon on Nov. 1, 1988. However, such splint devices tend to be complex and provide little selectivity as to the extent of mobility allowed the portion of the body to which they are applied. Other splints and similar devices are disclosed in the following U.S. Letters Patent:

| U.S. Pat. No. | Patentee(s) | Issue Date |
| --- | --- | --- |
| 1,716,221 | T. R. Fernie | June 4, 1929 |
| 1,726,728 | W. G. Adams | Sept. 3, 1929 |
| 3,117,786 | J. H. Anderson | Jan. 14, 1964 |
| 3,152,337 | G. D. Barry | Oct. 13, 1964 |
| 3,555,564 | E. Miskell, et al. | Jan. 19, 1971 |
| 3,581,740 | R. D. Sherbourne | June 1, 1971 |
| 3,605,120 | H. B. Hobbs | Sept. 20, 1971 |
| 3,779,550 | S. M. Benoun, et al. | Dec. 18, 1973 |
| 3,788,307 | H. M. Kistner | Jan. 29, 1974 |
| 3,903,878 | D. C. Spann | Sept. 9, 1975 |
| 3,911,497 | F. H. Lewis, Jr., et al. | Oct. 14, 1975 |
| 3,944,220 | T. Fasano | Mar. 16, 1976 |
| 4,041,940 | S. A. Frankel, et al. | Aug. 16, 1977 |
| 4,167,044 | L. E. Girard | Sept. 11, 1979 |
| 4,173,218 | P. S. Cronin | Nov. 6, 1979 |
| 4,183,098 | M. V. Knowles, Jr. | Jan. 15, 1980 |
| 4,417,570 | A. Finnieston | Nov. 29, 1983 |
| 4,451,044 | D. D. Elliot, Jr. | May 29, 1984 |
| 4,558,694 | L. M. Barber | Dec. 17, 1985 |
| 4,565,195 | J. H. Eisenberg | Jan. 21, 1986 |
| 4,573,456 | D. C. Spann | Mar. 4, 1986 |

-continued

| U.S. Pat. No. | Patentee(s) | Issue Date |
| --- | --- | --- |
| 4,675,914 | R. Mitchell | June 30, 1987 |
| 4,698,850 | E. E. Patton, Sr., et al. | Oct. 13, 1987 |
| 4,716,892 | S. Brunswick | Jan. 5, 1988 |
| 4,765,319 | A. Finnieston, et al. | Aug. 23, 1988 |
| 4,787,376 | J. H. Eisenberg | Nov. 29, 1988 |
| 4,798,199 | V. M. Hubbard, et al. | Jan. 17, 1989 |
| 4,807,609 | R. A. Meals | Feb. 28, 1989 |
| 4,883,073 | F. Aziz | Nov. 28, 1989 |
| 4,911,150 | M. D. Farley | Mar. 27, 1990 |
| 4,925,187 | C. R. Fleenor, et al. | May 15, 1990 |
| 4,954,925 | R. F. Garcia | Aug. 7, 1990 |
| 4,960,114 | C. L. Dale | Oct. 2, 1990 |
| 4,977,890 | D. B. Mann | Dec. 18, 1990 |

A number of these patents disclose devices which may be used for purposes other than therapy, rehabilitation, and/or aiding the physically impaired. For example, those patents issued to Fernie ('221), Adams ('728), Anderson ('786), Barry ('337), Hobbs ('120), Benoun ('550), Lewis ('497), Knowles ('098), Elliot ('044), Eisenberg ('195 and '376), Mitchell ('914), and Fleenor ('187) disclose devices to be used in particular sports in order to prevent injury. Each of these either provides for the rigid support of a selected portion of the body—typically the hand or foot—or provides a cushioning means for reducing the force of a blow which might otherwise cause physical damage. The Miskell ('564) patent discloses a glove for use by a surgeon, while the Garcia ('925) patent discloses a device for aiding in the placement of an intravenous tube into a patient.

Of the remaining patents which are related primarily to therapy, rehabilitation, and/or aiding the physically impaired, none discloses a device which may define varying flexibilities over the body thereof. Further, none provides for the retention of the selected body portion in a preselected position until force is exerted upon the device in an attempt to move the selected body portion.

Such devices are desirable especially with cerebral palsy patients, patients who have suffered strokes, and persons who have had tendon surgery. For many palsy patients, their hands are normally spasmed shut, and though they have muscular strength, they do not have the strength to open their hands. The same is true for stroke and arthritis patients. When held in the open position, however, the patient has the strength to close his hand, thereby allowing for the grasping and carrying of selected objects. By allowing such activity, many of these patients would be able function more normally, such as by feeding and clothing themselves.

For those recuperating from tendon surgery, such devices would also be desirable. Tendon surgery requires the tedious connection of the separated tendons and the careful stitching of the opening on the skin. Depending upon the function of the particular tendon, the associated digit or extremity must be retained in either the flexed or the contracted state in order to allow for better healing. As the healing process continues, more exercise may be accomplished without damage to the tendon. Conversely, exercise of the tendon will enhance the healing by preventing collagen formation and excessive scarring.

Typically, rigid casts and/or splints are used such as those disclosed in the cited prior art. These do not provide for the progressively increased exercise of the tendon. Devices such as casts do not allow for the observation of the healing process, as they are time consuming to remove and replace.

Therefore, an object of the present invention is to provide an improved splint/therapeutic device for at least partially immobilizing a portion of the body of a patient.

Another object of the present invention is to provide an improved splint/therapeutic device which allows the extent of immobility imparted to be preselected, and which allows such preselected extent of immobility to be varied over the surface area covered by the splint.

A further object of the present invention is to provide an improved splint/therapeutic device which is fabricated of an elastomeric material such that it can be trimmed to engage only that surface area of the patient's body where mobility is to be restricted.

Still another object of the present invention is to provide a splint/therapeutic device which defines a thickness that may be selectively thinned in order to allow for greater flexibility at subsequent stages in the healing process, thereby preventing the need for purchasing several devices to accomplish complete recovery.

Yet another object of the present invention is to provide an improved splint/therapeutic device which can also be used as a resistive exercise means.

Still a further object of the present invention is to provide an improved splint/therapeutic device which is inexpensive to manufacture.

DISCLOSURE OF THE INVENTION

Other objects and advantages will be accomplished by the present invention which provides an improved splint/therapeutic device for at least partially immobilizing a portion of the body of a patient and/or resistively exercising selected portions of a patient's body. The splint/therapeutic device comprises a splint body fabricated of a elastomeric material, the splint body having an inner surface for closely engaging a selected portion of the patient's body. Further, the splint body has a preselectively varying thickness, whereby the resistance to movement of the patient's body is correspondingly varied over the surface area of the body covered by the splint. The improved splint/therapeutic device also includes a suitable securing means for securing the splint on the body of the patient. In one preferred embodiment, such securing means includes adjustable securing straps which are received about the splint body and about the portion of the patient's body to which the splint is applied, and secured with hook-and-loop type fasteners.

BRIEF DESCRIPTION OF THE DRAWINGS

The above-mentioned features of the present invention will become more clearly understood from the following detailed description of the invention read together with the drawings in which:

FIG. 1 is a side elevational view of a prior art device used as a splint/therapeutic device;

FIG. 2 is a perspective view of an alternate embodiment of an improved splint/therapeutic device of the present invention;

FIG. 3 is a perspective view of an alternate embodiment of an improved splint/therapeutic device of the present invention;

FIG. 4 is a perspective view of an alternate embodiment of an improved splint/therapeutic device of the present invention;

FIG. 5 is a perspective view of an alternate embodiment of an improved splint/therapeutic device of the present invention;

FIG. 6 is an end view, in section, of the alternate embodiment of the improved splint/therapeutic device of the present invention as illustrated in FIG. 5;

FIG. 7 is a side view, in section, of the alternate embodiment of the improved splint/therapeutic device of the present invention as illustrated in FIG. 5;

FIG. 8 is a perspective view of an alternate embodiment of an improved splint/therapeutic device of the present invention;

FIG. 9 is an end view, in section, of the alternate embodiment of the improved splint/therapeutic device of the present invention as illustrated in FIG. 8;

FIG. 10 is an end view, in section, of the alternate embodiment of the improved splint/therapeutic device of the present invention as illustrated in FIG. 8;

FIG. 11 is an end view, in section, of the alternate embodiment of the improved splint/therapeutic device of the present invention as illustrated in FIG. 8;

FIG. 12 is a perspective view of an alternate embodiment of an improved splint/therapeutic device of the present invention;

FIG. 13 is a perspective view of an alternate embodiment of an improved splint/therapeutic device of the present invention;

FIG. 14 is a perspective view of a human hand which is spasmed in the closed position;

FIG. 15 is a perspective view of an alternate embodiment of an improved splint/therapeutic device of the present invention;

FIG. 16 is a perspective view of an alternate embodiment of an improved splint/therapeutic device of the present invention;

FIG. 17 is an end view, in section, of the alternate embodiment of the improved splint/therapeutic device of the present invention as illustrated in FIG. 16; and FIG. 18 is a perspective view of an alternate embodiment of an improved splint/therapeutic device of the present invention.

BEST MODE FOR CARRYING OUT THE INVENTION

An improved splint/therapeutic device incorporating various features of the present invention is illustrated generally at 10 in the figures. The splint 10 of the present invention is designed to partially or totally immobilize a portion of a patient's body, and/or to provide resistive exercise for muscle or tendon therapy to that portion of the patient's body. The splint 10 is designed to replace prior art devices such as that shown in FIG. 1, wherein a hooks 52 are affixed to a fingernail and a portion of the brace 50. A rubber band 54 is then stretched between the hooks 52 in order to prevent the finger from opening. This and other apparatuses may cause undue pain to the patient, or may otherwise be an unnecessary nuisance.

The splint 10 generally comprises a resilient splint body 12 which has an interior surface 14 for engaging a selected portion of the body of a patient. Preferably the splint body 12 is integrally molded of an elastomeric material, such as silicone rubber. Moreover, the splint body 12 is preferably molded such that the inner surface 14 is contoured, without the necessity of deformation through the application of pressure when worn, to closely engage a selected portion of the patient's body. The splint body 12 is also molded to closely engage a selected portion of the patient's body as it is disposed in a desired position such that the elastomeric body 12 biases such selected portion of the patient's body to the desired position. This desired position may be a position which promotes proper mending of bones, or healing of tendons or muscle tissue, or it may be the desired at rest position of the patient's body portion to overcome displacement caused by palsy or bone deformity.

The splint 10 can be fashioned to engage various parts of a patient's body, and to totally or partially immobilize such portions of the body of the patient. For example, in FIG. 2 an improved splint for the wrist 23 and hand 24 is illustrated at 10A. Hypothesizing injury to the finger 20, and presuming a desired patient body position in which the finger 20 is at least partially closed, the splint 10A has been molded such that the inner surface 14 conforms to the exterior contours of the lower arm 22 and finger 20 when in such desired position such that the resilient splint body 12 biases the finger 20 to the desired position.

It will be noted that in FIG. 2, the fingers 17-19 and the thumb 21 remain unrestricted. However, should the desired remedial position require, the splint body 12 can be molded to immobilize, or reduce the mobility of, the fingers 17-19, as illustrated in FIG. 3 in the embodiment labelled 10B. It is conceivable that a splint 10 may be molded to at least partially reduce the mobility of the thumb 21, as well. In this regard, it is contemplated that a splint 10 can be pre-molded to provide a preselected maximum area of restricted mobility and later trimmed to engage a lesser patient body area as may be required. For example, the splint of FIG. 3 can be premolded to the configuration of 10B and, prior to being secured on the body of the patient, trimmed to the configuration 10A such that the fingers 17-19 are not needlessly restricted. It will be appreciated that the use of a suitable elastomeric fabricating material, such as silicone rubber, permits the splint 10 to be easily trimmed using cutting instruments generally available to a physician in general practice. Such fabrication also permits the shaving of the splint 10 in order to reduce the thickness and enhance the flexibility, which will be appreciated in the progressive states of healing.

In order to secure the splint 10 to the body of the patient, a suitable securing means is provided. Such means can include adhesive or other suitable tapes, or various releasable straps. However, in the embodiment illustrated in FIG. 2, the splint 10A includes one or more adjustable straps 26 which are received around the associated patient's body part and around the splint 10, and adjustably secured with a hook-and-loop fastener such as the illustrated hook-and-loop type fastener 28, as best illustrated in FIG. 4. It will be appreciated that the straps 26 allow the splint 10 to be quickly and easily secured or removed, and the tightness of the straps 26 can be easily adjusted to provide for a comfortable fit. Of course, the number and placement of the straps 26 will vary depending upon the configuration of the splint 10 and the portion of the patient's body to which it is to be secured, as is reflected in the figures.

The securing means can also comprise patient body encircling portions integrally formed with the splint body 12 if desired. For example, in the embodiments of FIG. 15 the straps 26' are integrally formed with the splint body 12, thereby obviating the need for separate securing means. Of course, this can be accomplished by molding the straps 26' during the initial manufacturing process.

The splint 10 typically defines openings 32 such that the overall weight of the splint 10 is reduced and further to provide for the aeration, temperature control, and moisture control of the selected body portion to which it is secured. The openings 32 are defined at selected locations which do not carry substantial tensile or compressive loads placed upon the splint 10, the loads normally exerted at those locations being distributed to adjacent portions of the splint 10.

In FIG. 4, the splint 10C is molded to bias the hand 24, and the fingers 17-20 and thumb 21 to a fully opened position. The splint 10C will allow for the relaxation of the extensor tendons after surgical repair of the same. When the extensor tendons begin to heal, exercise may be gradually increased. Early mobilization, as has been discussed, will promote more rapid healing.

FIG. 5 illustrates a similar embodiment to that of FIG. 4. However, the splint 10D biases the wrist in a position further back than the splint 10C. Due to the nature of the preferred material for construction, the splint 10D may be attained by heating a splint 10C until malleable, and then by molding the splint 10C to the selected position. FIG. 5 is illustrative of the numerous configurations in which the present splint 10 may disposed. FIG. 6 illustrates a cross-sectional view of the splint 10D wherein a plurality of ribs 34 are defined which are greater in thickness than the lateral portions 36 of the splint body 14. The ribs 34 provide for the at least partial immobilization of the fingers 17-20 and thumb 21, while the thinner lateral portions 36 maintain the relative positions of the ribs 34, the reduced thickness aiding in minimizing the weight of the splint 10D.

The amount of resistance to movement imparted by the splint 10 is preselectively controlled by varying the thickness of the splint body 12. It will be understood by those skilled in the art that the force necessary to deform the elastomeric material of the body 12, such material typically being of substantially uniform density, increases with the thickness of such material. Therefore, the splint body 12 is provided with one or more portions or areas having increased thicknesses to produce a greater resistance to movement of the patient's body proximate that area. This is best illustrated in FIG. 6 where the body 12 of the splint 10 is provided with a portion of increased thickness 30 which engages the patient's body beneath the wrist 23 thereby increasing the resistance to motion at the wrist 23 relative to the other areas of engagement.

Of course, if greater wrist mobility is desired, the thickness of the splint body 12 at the portion 30 can be decreased. This can be accomplished by pre-molding the splint 10D with a thinner portion 30 or by cutting away the fabricating material to produce a thinner portion 30. Thus, with respect to the degree of mobility of various other selected body portions can be controlled by providing the body 12 with the appropriate thickness at the portion of the splint body 12 which engages the selected body portion.

It will be recognized by those skilled in the art that the resistance to patient mobility provided by the splint apparatus 10 allows the splint 10 to be utilized to resistively exercise muscles and tendons. Moreover, by selectively varying the thickness of the resilient body 12, the resistive exercise provided can be selectively apportioned to the various patient body portions to which the splint is applied. With respect to the splint 10D of FIG. 5, for example, damage to the wrist 32 may call for the thickness of the ribs to be substantial in order to immobilize the wrist 32, but it may be desirable to provide resistive exercise to the fingers 17-20 and the thumb 21 to avoid atrophy of the muscle tissue. Thus, the ribs can be molded to define a lesser thickness proximate the fingers 17-20 and thumb 21 so as to allow movement of the fingers 17-20 and thumb 21 against the bias of the body 12, thereby exercising the operatively associated muscles. Further, as the healing process continues, it may be desirable to provide some mobility to the wrist 23 of the patient, and commence rehabilitation of the operatively associated muscles and tendons. This can be accomplished by reducing the thickness of the ribs 34 proximate the wrist 23.

As noted above, the splint 10 can be applied to various parts of a patient's body and further examples of various applications are illustrated in FIGS. 8-19, which are primarily used for restraining the fingers 17-20 and the thumb 21. FIG. 8 illustrates a straight splint 10E which may be used to retain a finger as shown. In the preferred embodiment shown, ribs 34 are integrally formed with lateral portions 36 encircling the finger, with openings 32 defined therebetween for the clearance of the knuckles. As shown in the cross-sectional views of FIGS. 9-11, the thickness of the ribs 34 may be varied from one end to another. The embodiment shown is thicker toward the palm, thereby allowing for greater flexibility at the end of the finger as opposed to the flexibility at the base. In FIG. 12, an L-shaped splint 10F is illustrated for reducing the mobility of a finger.

FIG. 13 illustrates a U-shaped splint 10G for biasing the thumb and forefinger to selected positions. Such an embodiment may be desired in cases such as that illustrated in FIG. 14, which depicts the position of a hand 24 crippled with arthritis, palsy, or other similar disablement which causes a spasmed closed hand.

The splints 10H, 10I and 10J of FIGS. 15, 16 and 18, respectively, depict splints for restricting the mobility of a plurality of the fingers 17-20 and the thumb 21. The splint 10H may be used to at least partially immobilize the fingers 17-20 independently one from the other. The finger retaining portions are similar to the splint 10E described above and depicted in FIG. 8.

The splint 10I as shown may be used to at least partially immobilize the fingers equally. FIG. 17 illustrates a cross-sectional view of the splint 10I wherein ribs of varying thicknesses are incorporated. The ribs may be selectively cut along the centerlines 35 shown in order to allow for the independent mobilization of selected fingers.

The splint 10J shown in FIG. 18 is similar to the splint 10I shown in FIG. 16. However, the splint 10J as shown will allow for the complete mobility of the finger 20 and the thumb 21. This embodiment may be achieved by trimming the respective portions of the splint 10I which would otherwise at least partially immobilize the finger 20 and the thumb 21.

It is envisioned that other embodiments may be developed to at least partially immobilize various other selected body portions than herein described. For example, a splint 10 may be used to partially immobilize an elbow, knee, or foot. In these embodiments, the same subject matter herein disclosed may be adapted to achieve similar results for the selected body portions.

In light of the above, it will be recognized that the present invention provides an improved splint with great advantages over the prior art. Unlike conventional splints, the splint 10 allows the physician to preselect the extent to which the patient's body is immobilized, and a splint 10 can impart greater immobility to certain portions of the patient's body which it contacts than others. The ability to trim the splint 10 to fit the particular injury or application makes it more versatile than conventional splints and obviates the need for various different splint configurations for the same general body portion. This ability to trim the splint 10 also allows openings to be cut in the body 12 of the splint to provide access to lacerations without compromising the immobilization of the patient's body portion. The splint 10 can be used to immobilize, or partially immobilize, bone fractures, or damaged tendons or muscles, and can also be used as to resistively exercise muscles and/or tendons to overcome or prevent atrophy of such tissues. Moreover, the splint 10 can be used as a brace for correcting or reorienting deformities of various portions of a patient's body. For example, patients with radial nerve damage ("wrist drop") can utilize the splint to reorient the affected hand to a natural position. Similarly, the splint 10 can be used to reorient hands mishappened by osteoarthritis.

While a preferred embodiment has been shown and described, it will be understood that there is no intent to limit the invention to such disclosure but rather it is intended to cover all modifications and alternate constructions falling within the spirit and scope of the invention as defined in the appended claims.

I claim:

1. A splint/therapeutic device for biasing a selected body portion of a patient to a preselected position and for providing at least partial limited mobility of said selected body portion, said device comprising a splint body integrally fabricated of a resilient material and preformed to restrain said body portion in said preselected position, said splint body having an inner surface that has preselectively contoured areas within said material of said splint body, without the necessity of deformation thereof, to closely conform to and engage said body portion as said body portion is in said preselected position, said splint body defining a preselected thickness when in an uncompressed state to achieve a preselected degree of bending of said splint body by resiliency of said splint body material and thereby said at least partial limited mobility of said body portion, whereby said resilient material of said splint body biases said portion of said selected body portion to said preselected position, said preselected thickness varying along a length and width of said splint body.

2. The splint/therapeutic device of claim 1 wherein said splint body is fabricated of an elastomeric material.

3. The splint/therapeutic device of claim 1 wherein said device further comprises securing means for securing said splint body to said portion of said patient's body.

4. The splint/therapeutic device of claim 3 wherein said securing means comprises at least one securing strap for being received about said splint body and said portion of said patient's body, said securing strap being provided with adjustable fastening means for securing said strap in position about said splint body and said portion of said patient's body.

5. The splint/therapeutic device of claim 4 wherein said fastening means includes a hook and loop fastener.

6. The splint/therapeutic device of claim 3 wherein said securing means includes a patient body encircling portion integral with said splint body.

7. The splint/therapeutic device of claim 3 wherein said securing means includes at least one strap integrally formed with said splint body.

8. The splint/therapeutic device of claim 1 wherein said selected body portion of said patient is one of the extremities, said extremities including the hands and the feet of said patient.

9. The splint/therapeutic device of claim 1 wherein said selected body portion of said patient is one of the extremities, said extremities including the hands and the feet of said patient.

10. A splint/therapeutic device for biasing a selected body portion of a patient to a preselected position and for providing at least partial limited mobility of said selected body portion, said device comprising:

a splint body integrally fabricated of a resilient material and preformed to restrain said body portion in said preselected position, said splint body having an inner surface that has preselectively contoured areas within said material of said splint body, without the necessity of deformation thereof, to closely conform to and engage said body portion as said body portion is in said preselected position, said splint body defining a preselected thickness to achieve a preselected degree of bending of said splint body and thereby said at least partial limited mobility of said body portion, and whereby said resilient material of said splint body biases said body portion of said selected body portion to said preselected body position, said preselected thickness varying along a length and width of said splint body; and securing means for securing said splint body to said selected body portion.

11. The splint/therapeutic device of claim 10 wherein said splint body is fabricated of an elastomeric material.

12. The splint/therapeutic device of claim 10 wherein said elastomeric material comprises silicone rubber.

13. The splint/therapeutic device of claim 10 wherein said securing means comprises at least one securing strap for being received about said splint body and said portion of said patient's body, said securing strap being provided with adjustable fastening means for securing said strap in position about said splint body and said portion of said patient's body.

14. The splint/therapeutic device of claim 13 wherein said fastening means includes a hook and loop fastener.

15. The splint/therapeutic device of claim 10 wherein said securing means includes a patient body encircling portion integral with said splint body.

16. The splint/therapeutic device of claim 10 wherein said securing means includes at least one strap integrally formed with said splint body.

17. The splint/therapeutic device of claim 10 wherein said selected body portion of said patient is one of the extremities, said extremities including the hands and the feet of said patient.

18. A splint/therapeutic device for biasing a selected body portion of a patient to a preselected position and for providing at least partial limited mobility of said selected body portion, said device comprising:

a splint body integrally fabricated of an elastomeric material and preformed to restrain said body portion in said preselected position, said splint body having an inner surface that has preselectively contoured areas within said material of said splint body to closely conform to and engage said body portion as said body portion is in said preselected position without deformation of said elastomeric material, said splint body defining a substantially uniform density with areas of varying thickness when in an uncompressed state to achieve a preselected degree of bending of said splint body and thereby said at least partial limited mobility of said body portion, and whereby said elastomeric material of said splint body biases said body portion to said preselected position, said preselected thickness varying along a length and width of said splint body; and securing means for securing said splint body to said selected body portion.

* * * * *